US006181966B1

(12) United States Patent
Nigam (10) Patent No.: US 6,181,966 B1
(45) Date of Patent: Jan. 30, 2001

(54) HEART THERAPY APPARATUS WITH THERAPY CORRECTION MEANS

(75) Inventor: Indra B. Nigam, Lake Oswego, OR (US)

(73) Assignees: Biotronik Mess- und Therapiegeräte GmbH & Co.; Ingenieurbüro, both of Berlin (DE)

( * ) Notice: Under 35 U.S.C. 154(b), the term of this patent shall be extended for 0 days.

(21) Appl. No.: 09/220,755

(22) Filed: Dec. 28, 1998

(51) Int. Cl.[7] ................................................ A61N 1/39
(52) U.S. Cl. ........................ 607/4; 607/5; 607/2; 607/14
(58) Field of Search ...................... 607/14, 4, 5, 9, 607/2

(56) References Cited

U.S. PATENT DOCUMENTS

| 4,830,006 | * | 5/1989 | Haluska et al. ................ 607/14 |
| 5,002,052 | * | 3/1991 | Haluska ........................ 607/14 |
| 5,836,971 |   | 11/1998 | Starkweather . |

FOREIGN PATENT DOCUMENTS

| 0360412A1 | 3/1990 | (EP) . |
| 0538996A1 | 4/1993 | (EP) . |
| 0580128A2 | 1/1994 | (EP) . |

* cited by examiner

Primary Examiner—Kennedy Schaetzle
(74) Attorney, Agent, or Firm—Venable; George H. Spencer; Robert Kinberg (57) ABSTRACT

A heart therapy apparatus (1) with detection means (3, 5, 9) for detecting a physiological parameter that characterizes the state of the heart/circulatory system, with comparison value storage means (17), comparator means (15) for comparing the detected values to the stored values, therapy storage means (23) for storing a plurality of potential therapies, therapy means (25) for selectively realizing one of the potential therapies, with therapy registration means (27) for registering a realized therapy, and therapy selection means (19) for selecting one of the stored therapies and activating the therapy means in dependence on the classification signal and the memory content of the therapy registration means. In addition therapy correction means (21) are provided for delaying or inhibiting the realization of a therapy associated with the classification signal, or any therapy at all, or for changing the therapy coordinated with the classification signal in dependence on the classification signal and the memory content of the therapy registration means.

9 Claims, 2 Drawing Sheets

HEART THERAPY APPARATUS WITH THERAPY CORRECTION MEANS

The invention relates to a heart therapy apparatus comprising: detection means for detecting a physiological parameter that characterizes the state of the heart/circulatory system; comparison value storage means for storing a plurality of comparison values for the physiological parameter; comparator means, which are connected on the input side to the detection means and the comparison value storage means, for comparing the detected values to the stored values and for issuing a classification signal as a result of the comparison; therapy-storage means for storing a plurality of potential therapies for a heart (H); therapy means for selectively realizing one of the potential therapies; therapy registration means for registering a therapy that has been realized; and, therapy selection means, which are connected on the input side to the output of the comparator means and the therapy registration means, for selecting one of the stored therapies and activating the therapy means in dependence on the classification signal and the storage content of the therapy registration means.--.

Arrhythmias are known to manifest themselves in an extraordinary number of different forms. In recent years, an essential portion of the efforts spent on research and development in the field of implantable pacemakers and defibrillators was dedicated to the reliable detection of qualitatively different arrhythmias, requiring different therapies, and to the coordination of these with therapies that are adequate for the actual conditions.

The most important criteria for differentiating between different arrhythmia conditions continue to be the rate criteria, meaning the level and, if necessary, also the development over time (stability, monotony, etc) of the frequency of ventricular and atrial cardiac actions. Increasingly, additional data concerning the condition and/or the case history of the patient are also taken into account to arrive at an adequate therapy based on the rate criteria.

Thus, in the EP 0 580 128 A2, the rate criteria for the pacemaker therapy of pathological tachycardias are modified in dependence on a status signal that characterizes the actual physical activity of the patient and is obtained by means of an activity sensor. The respective algorithm is invalidated when primary atrial fibrillation is detected.

With a combination cardioverter/defibrillator (ICD= implantable cardioverter/defibrillator) and pacemaker unit, as disclosed in the EP 0 360 412 A1 (in continuation of a classification model with rigid range limits), the heart rate continuum is subdivided into several sub-ranges with variable limits. The actually used therapy for the limit ranges is selected from a store of therapies, which are predetermined for specific sections, by taking into account the case history, specifically the preceding rate development over time.

It is suggested in the EP 0 538 996 A1 that a different rate criterion be used for the initial detection of a tachyarrhythmia be different than that used for a confirmation detection at a later point in time. This is designed to take into account the physiological findings that (1) tachyarrhythmias that basically require therapy will relatively often end spontaneously and without stimulation intervention, but that (2) therapy will increasingly become necessary with longer-lasting tachycardias.

The reference U.S. Pat. No. 5,836,971 of the generic type proposes that various rate ranges for an ICD are dynamically associated with various therapies, which differ in the amount of energy used, in dependence on whether a previous therapy attempt took place and the level of energy used for this attempt. This is designed to ensure implementation of the principle of using increasing energy amounts during successive therapy attempts, even if a lower rate than the previous one adjusts itself following a shock, without the heart having returned to the normal sinus rhythm.

It is the object of the invention to provide an improved heart therapy apparatus of the generic type, which permits a more careful therapy of tachyarrhythmias.

SUMMARY OF THE INVENTION

The above object is solved according to the present invention with a heart therapy apparatus that comprises: detection means for detecting a physiological parameter that characterizes the state of the heartcirculatory system; comparison value storage means for storing a plurality of comparison values for the physiological parameter; comparator means, which are connected on the input side to the detection means and the comparison value storage means, for comparing the detected values to the stored values and for issuing a classification signal as a result of the comparison; therapy-storage means for storing a plurality of potential therapies for a heart (H); therapy means for selectively realizing one of the potential therapies; therapy registration means for registering a therapy that has been realized; therapy selection means, which are connected on the input side to the output of the comparator means and the therapy registration means, for selecting one of the stored therapies and activating the therapy means in dependence on the classification signal and the storage content of the therapy registration means; and, therapy correction means that are coordinated with the therapy selection means for delaying or inhibiting the realization of a therapy associated with the classification signal, or any therapy at all, or for changing the therapy associated with a classification signal in dependence on the classification signal and the memory content of the therapy registration means in claim 1.

The invention includes the realization that changes in a variable characterizing the heart condition, particularly heart rate changes, following a therapy attempt for determining the further therapy course should be evaluated differently, even if the therapy attempt did not result in a return to the normal condition. Particularly when detecting specific changes, it may be appropriate to turn away from the principle of electrotherapy with increasing energy use or to stop further therapy attempts.

For an ICD, for example, it means that when detecting a rate drop following a defibrillator shock, no further therapy attempts will take place, even if the rate is still within a tachycardia range to which a therapy is assigned.

The invention provides for means to detect a physiological parameter, which characterizes the condition of the heart/circulatory system, for storing a multitude of comparison values for the physiological parameter and for comparing the detected values with the stored values in order to issue a classification signal. The invention also includes existing means for storing a plurality of potential therapies, means for selectively realizing one of the potential therapies, means for registering a previously realized therapy, and means for selecting one of the stored therapies in dependence on the classification signal. Special means are provided here for delaying the implementation of or for inhibiting the therapy associated with the actually present classification signal—or any therapy—in dependence on the classification signal and the previously executed therapy (to be more exact: a therapy attempt).

A special embodiment of the therapy apparatus, an implantable cardioverter/defibrillator (ICD) or combination pacemaker/defibrillator, comprises a shock pulse generator for the cardioversion or the defibrillation of the heart. Following a preceding shock pulse, it is designed to delay or inhibit additional shock pulses upon receiving a first classification signal, which indicates a heart rate with increased sinus rhythm. (With a combination pacemaker/defibrillator, it is possible in that case to activate an anti-tachycardia stimulation as well. However, this may not make sense physiologically.) The apparatus is otherwise designed to trigger additional shock pulses with essentially the same energy level, following an initial pulse, when receiving a second classification signal, which specifically indicates a heart rate in the tachyarrhythmia range, meaning above the range of increased sinus rate, but below the fibrillation limit.

In view of the special importance of the rate criteria for heart therapy apparatuses according to the invention, a detection of the actual heart in particular—if necessary also a determination of the criteria characterizing its development over time—is generally provided, so that the classification signal characterizes the association of the cardiac activity with the predetermined rate range.

In order to realize the invention, at least two invariable comparison values must be preprogrammed for the heart rate. With this, each of at least three classification signals characterizes the association of the actual heart rate with respectively one invariant, predetermined rate range, at least one of which is defined as hysteresis range in dependence on the therapy case history. However, it is preferable if three or four comparison values are preprogrammed, so that each of four or five classification signals characterizes the association of the actual heart rate to respectively one rate range, two of which are defined as upper or lower hysteresis range.

Advantageous modifications of the invention are otherwise characterized in the dependent claims or are shown in further detail in the following together with the description of the preferred embodiment of the invention and with the aid of the Figures.

BRIEF DESCRIPTION OF THE DRAWINGS

Shown are.

DETAILED DESCRIPTION OF THE PREFERRED EMBODIMENTS

Figure 1:
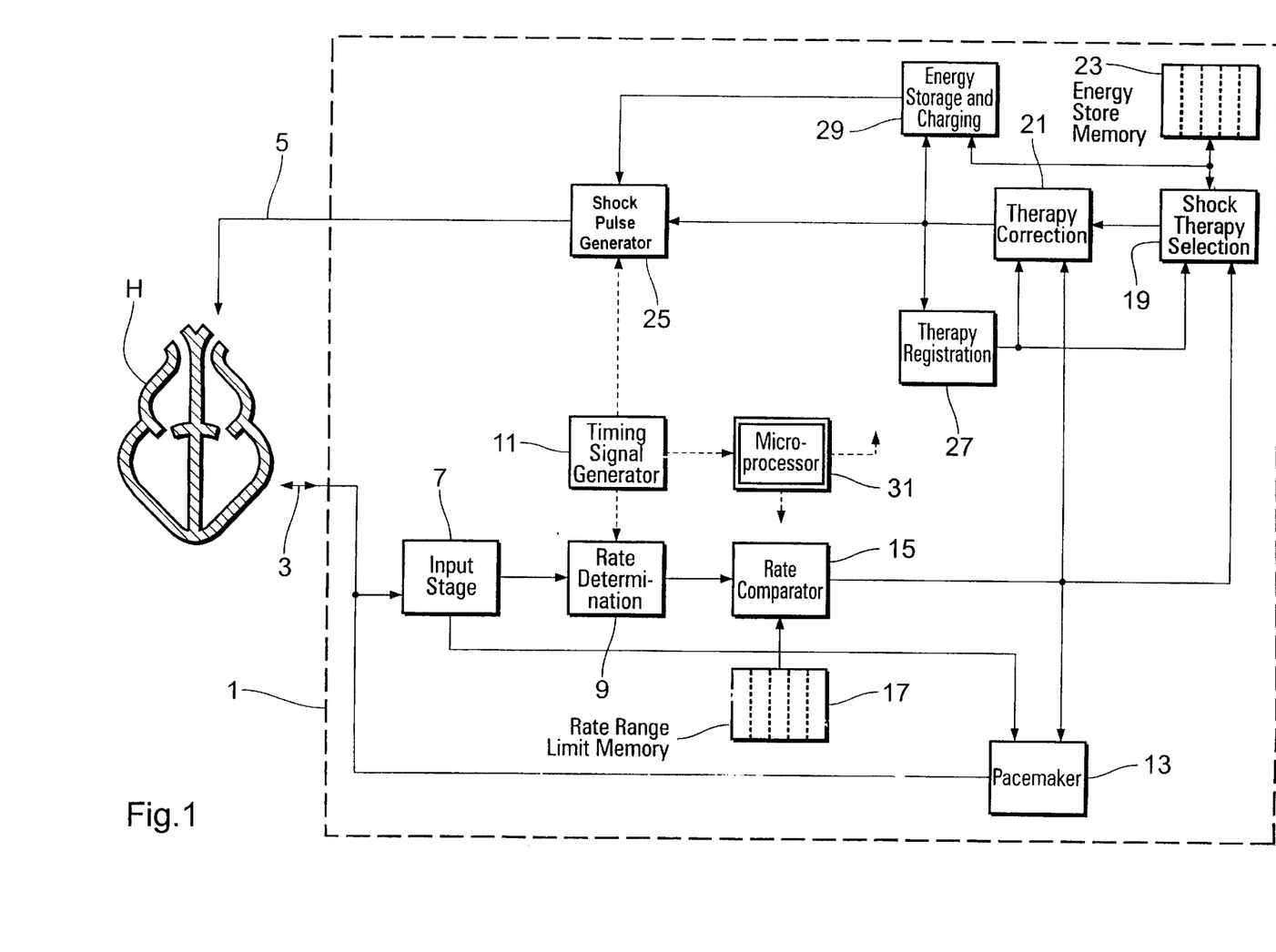
FIG. 1 A diagram of the operational connections for a combination defibrillator/pacemaker as preferred embodiment of a device according to the invention, and FIG. 2 A graphic representation as explanation for the operating mode of the device according to FIG. 1.

FIG. 1 shows, as functional block diagram, a very simplified representation, which is limited to the components essential to the invention, for an implantable defibrillator/pacemaker 1, which is connected to the heart H of a patient via a sensing and stimulation electrode lead 3 and a defibrillation electrode lead 5.

The sensing and stimulation electrode lead 3 is connected on the input side with a heart signal input stage 7. On the one hand, this stage is connected on the output side to a rate determination stage 9 that additionally receives timing signals from a timing signal generator 11 and, on the other hand, to a signal input for a pacemaker unit 13. The rate determination stage 9 is connected on the output side with an input for a multi-stage rate comparator 15, which is in turn connected via a second input to a rate range limit memory 17.

The rate comparator 15 output is connected to a control input of the pacemaker unit 13 and also with respectively one input of a shock therapy selection unit 19, as well as a downstream connected therapy correction stage 21. The shock therapy selection unit 19 is furthermore connected to an energy stage memory 23 and, on the output side, to an additional input of the therapy correction stage 21. This stage is finally connected on the output side to a shock pulse generator 25, the actual defibrillator stage, and via a signal lead also to a therapy registration stage 27. The defibrillator stage 25 is connected via the defibrillation lead 5 to the heart H and is fed from an energy storage and charging stage 29, which is itself connected on the input side to an energy stage memory 23 and the output of the therapy correction stage 21.

A microprocessor control 31 controls the total operation of this arrangement. The apparatus operates as follows:

Following standard processing in the input stage 7, the relevant heart rate for the control, that is to say preferably the ventricular rate, but also the atrial rate if necessary, is determined from the signals scanned endocardially at the heart and the internally provided timing signals. Subsequently, this rate is subjected in the rate comparator 15 to a comparison with preprogrammed rate range limits that are stored in the rate range limit memory 17. In this way, it is determined in which diagnostically relevant rate range the cardiac activity is actually located. Further details can be found below.

As a result of this comparison, the rate comparator emits a classification signal, which is transmitted as a critical control signal simultaneously to the pacemaker unit 13, the shock therapy selection unit 19 and the therapy correction stage 21. Depending on the type of classification signal, either a stimulation operation of the pacemaker unit 13 or a defibrillator operation is controlled—in the standard way, with additional control through the input stage 7 output signal—or the device does not have a therapeutic effect.

With respect to the defibrillator component, one of several preprogrammed shock therapy modi, which are stored in the memory 23, is selected if necessary in response to the classification signal by the shock therapy selection unit 19 in accordance with criteria that are explained in further detail in the following. A corresponding control signal is transmitted to the therapy correction stage 21 as well as to the energy storage and charging stage 29 where the necessary shock energy is made available in the standard way.

A post-processing of the control signal emitted by the shock therapy selection unit 19 occurs in the therapy correction stage 21 with the aid of the classification signal from the rate comparator 15 and an output signal from the therapy registration stage 21 that characterizes the preceding therapy (-ies), thereby taking into account the therapy case history. As a result of this post-processing and in dependence on the concrete classification signal in particular, the modus "defibrillation shock" is either maintained, insofar as it was adjusted, or any shock therapy is inhibited. The selection of a different modus during the preceding therapy step means that the result of the post-processing can be subject to different marginal conditions, or the therapy correction stage 21 is activated for a subsequent testing and therapy phase only through the selection of this modus. Finally, the shock pulse generator 25 is activated or inhibited and a shock pulse transmitted to the heart or suppressed by the output signal from the therapy correction stage 21, that is to say at the completion of the charging of the energy memory (not specially shown here).

At a predetermined later point in time, a renewed evaluation and decision cycle is controlled by the microprocessor control 31, which can either be executed as described in the above or can be modified, in particular, to the effect that after a longer interval, a different operational mode is selected by the therapy correction stage 21, or this stage is deactivated, so that the therapy selection again becomes independent of the therapy case history, especially the temporary application of a defibrillation shock.

Figure 2:
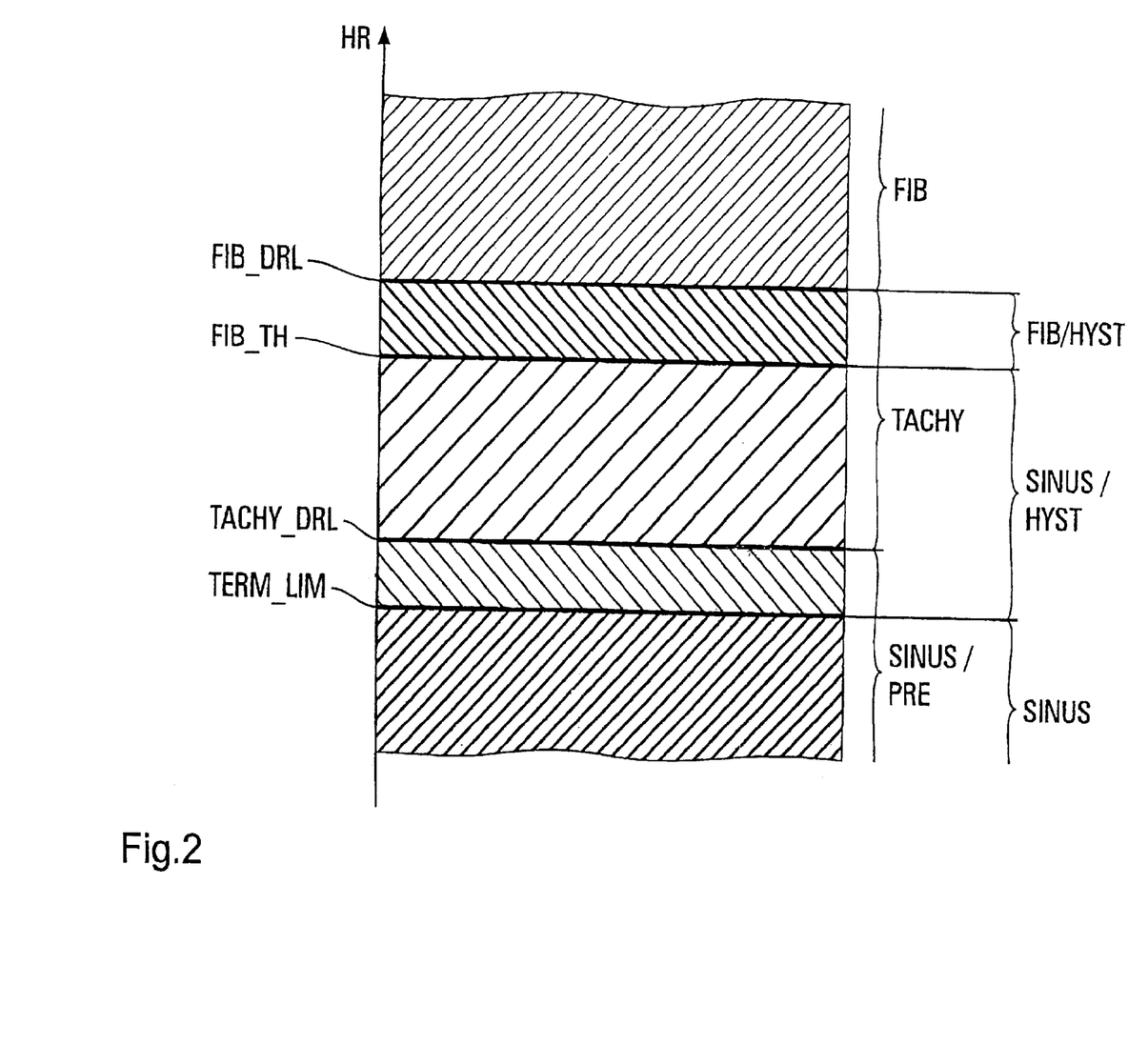

FIG. 2 contains a schematic representation of the heart rate continuum (with increasing rate values HR in the direction of the y-axis) with the rate range limits FIB__DRL (rate limit between tachycardia and fibrillation range), FIB__TH (lower rate limit for post-shock defibrillation therapy), TACHY__DRL (rate limit between sinus rate range and tachycardia range), TERM__LIM (upper rate limit value for a defibrillation that is considered successful). As can be seen in the Figure, the rate range limits define the rate ranges FIB, FIB/HYST (only defined following a shock pulse), TACHY (only defined before a shock pulse), SINUS/HYST (only defined after a shock pulse) and SINUS/PRÄ (only defined before a shock pulse) and SINUS (only defined after a shock pulse), wherein it must be taken into account that the hysteresis ranges FIB/HYST and SINUS/HYST are defined in different ways:

The upper hysteresis range FIB/HYST comprises only a (upper) partial range of the TACHY range—which is quasi divided following a defibrillation shock for the rate evaluation in order to determine the continued therapy—whereas the lower hysteresis range SINUS/HYST comprises a (upper) partial range of the range SINUS/PRÄ, defined prior to a shock, and the total remaining TACHY range.

With an embodiment that is simplified to make evaluation easier, the limits TACHY__DRL and TERM__LIM and thus also the ranges SINUS/PRÄ and SINUS coincide, so that the lower hysteresis range SINUS/HYST alone corresponds to the lower tachycardia partial range.

For the rate diagram shown, a defibrillation therapy is triggered when the rate is in the FIB range. The distinction between the ranges SINUS/PRE and TACHY is only relevant for a combination anti-tachycardia pacemaker/defibrillator where a rate in the TACHY range—prior to a shock pulse—triggers an anti-tachycardia stimulation, e.g. an overdrive or orthorhythmic stimulation (known per se).

If the rate drops into the SINUS range, following a defibrillation shock, the defibrillation therapy is successfully concluded. A standard monitoring operation is normally resumed in that case.

If the rate drops only to the SINUS/HYST range, continued special monitoring is advised, to be sure, but no further shock pulses are applied because it is assumed that the heart has changed in a physiologically favorable way from the fibrillation state to the sinus activity state with increased frequency. (By the way, it does not make sense to determine that a therapy must be stopped completely in this rate range because a tachycardia would then be detected later on—in the normal pre-shock detection mode—and, with a combination anti-tachycardia pacemaker/defibrillator, an anti-tachycardia stimulation would be initiated in a physiologically unsuitable manner.)

However, if the rate drops only slightly into the FIB/HYST range, then the normal shock therapy is continued—in the same way of course as when it remains in the FIB range—provided no other limitation is effective here.

The invention in its embodiment is not limited to the aforementioned, preferred exemplary embodiment. Rather, a number of variants are possible, which make use of the presented solution in different types of embodiments.

Thus, the heart therapy apparatus—with a basically identical analysis of the heart rate—can also be configured as a dosing instrument for medications or as a nerve stimulator—in particular for the vagus stimulation—or as a combination nerve stimulator/pacemaker for a fibrillation therapy requiring medications or neuro-stimulation.

It is also possible to provide means for differentiating between a higher number of cardiac rate ranges. Furthermore, the classification of the cardiac activity does not have to occur or not primarily on the basis of the absolute values for the heart rate or its development over time, but can include in particular an analysis of the endocardially detected heart signal (IECG) morphology. To be sure, under some circumstances and with suitable signal processing, the signal morphology is a usable criterion, e.g. for distinguishing between the sinus activity on the one hand and (a continuation of the shock therapy requiring) tachyarrhythmias on the other hand.

What is claimed is:

1. A heart therapy apparatus, comprising:
   detection means for detecting a physiological parameter that characterizes the state of the heart/circulatory system,
   comparison value storage means for storing a plurality of comparison values for the physiological parameter,
   comparator means, which are connected on the input side to the detection means and the comparison value storage means, for comparing the detected values to the stored values and for issuing a classification signal as a result of the comparison,
   therapy-storage means for storing a plurality of potential therapies for a heart (H),
   therapy means for selectively realizing one of the potential therapies,
   therapy registration means for registering a therapy that has been realized,
   therapy selection means, which are connected on the input side to the output of the comparator means and the therapy registration means, for selecting one of the stored therapies and activating the therapy means in dependence on the classification signal and the storage content of the therapy registration means, and
   therapy correction means that are coordinated with the therapy selection means for delaying or inhibiting the realization of a therapy associated with the classification signal, or any therapy at all, or for changing the therapy associated with a classification signal in dependence on the classification signal and the memory content of the therapy registration means.

2. A heart therapy apparatus according to claim 1, wherein the therapy means comprise a shock pulse generator for generating shock pulses for the cardioversion or defibrillation of the heart and, following a shock pulse, the therapy correction means delay or inhibit additional shock pulses upon receiving a first classification signal.

3. A heart therapy apparatus according to claim 1, wherein the therapy means comprise a shock pulse generator for generating shock pulses for the cardioversion or defibrillation of the heart and that following a shock pulse, the therapy correction means trigger further shock pulses with essentially the same energy level upon receiving a second classification signal.

4. A heart therapy apparatus according to claim 1, wherein the detection means detect at least the heart rate; and the comparison value storage means store a plurality of heart rate comparison values, such that the classification signal characterizes the coordination of the actual heart rate with a predetermined rate range.

5. A heart therapy apparatus according to claim 2, wherein the first classification signal characterizes a heart rate in the increased sinus rhythm range, below a predetermined tachycardia rate limit.

6. A heart therapy apparatus according to claim 3, wherein the second classification signal characterizes a heart rate in a tachycardia range that is above a tachycardia rate limit.

7. A heart therapy apparatus according to claim 6, wherein the tachycardia range characterized by the second classification signal is located below a fibrillation rate limit.

8. A heart therapy apparatus according to claim 4, wherein at least two comparison values of the heart rate are fixedly pre-programmed, such that each of at least three classification signals characterizes the coordination of the actual heart rate to respectively one invariant predetermined rate range, and wherein at least one rate range is defined as a hysteresis range in which the therapy correction means are effective, depending on the therapy case history.

9. A heart therapy apparatus according to claim 8, wherein four comparison values of the heart rate are fixedly pre-programmed, such that each of the five classification signals characterizes the coordination of the actual heart rate with respectively one predetermined rate range and, wherein two rate ranges are defined as hysteresis ranges in which the therapy correction means are effective.

* * * * *

UNITED STATES PATENT AND TRADEMARK OFFICE
CERTIFICATE OF CORRECTION

PATENT NO.    : 6,181,966 B1
DATED         : February 6, 2001
INVENTOR(S)   : Donald M. Gray et al.

It is certified that error appears in the above-identified patent and that said Letters Patent is hereby corrected as shown below:

On title page,
IN THE REFERENCES CITED

On page 1, delete "Kiessling, L.L., et al., "Flanking Sequence effects within the Pyrimidine Triple-Helix Motif Characterized by Affinity Clearing," *Biochemistry*, 31:2829-2834", add --Kieslling, L.L., et al., "Flanking Sequence Effects within the Pyrimidine Triple-Helix Motif Characterized by Affinity Clearing," *Biochemistry*, 31:2829-2834, 1992.--.

Column 8:
Line 20, delete "pp.22-23", insert -- columns 14-15 --.

Column 8:
Line 28, after "HYBsimulator", delete "used", insert -- referred to--.

Column 8:
Line 37, delete "pp.24-25", insert -- column 16, equations 1,2, and 3

Column 10:
Line 31, delete "αG", insert -- ΔG --.

Column 10:
Line 32, delete "αG", insert --ΔG --.

Column 15:
Line 45, above "r(AG):r(CU)", insert heading -- RNA:RNA Duplex --.

Column 15:
Line 49, above "d(AG):r(CU)", delete "DNA:DNA Hybrid", insert -- DNA:RNA Hybrid --.

Column 15: line
Line 53, above "r(AG):d(CT)", insert heading -- RNA:DNA Hybrid --.

UNITED STATES PATENT AND TRADEMARK OFFICE
CERTIFICATE OF CORRECTION

PATENT NO. : 6,181,966 B1
DATED : February 6, 2001
INVENTOR(S) : Donald M. Gray et al.

It is certified that error appears in the above-identified patent and that said Letters Patent is hereby corrected as shown below:

Column 19:
Line 13, delete "Tm (r(ACU):S-d(AGT)$_8$)", insert --Tm (r(ACU)$_8$:S-d(AGT)$_8$ --.

Column 19:
Line 18, delete "52.4", insert -- 52.2 --.

Column 22:
Table 8, delete "f(Dtc), insert -- f(dTC) --.

Column 32:
Line 29, table 16, below "Example sets of independent triplex DNA:DNA:DNA.", delete duplicate line "Example sets of independent triplex DNA:DNA:DNA."

Column 33:
Line 4, table 16, below "Example sets of independent triplex DNA:DNA:DNA.", delete duplicate line "Example sets of independent triplex DNA:DNA:DNA."

Column 37:
Line 22, delete "-9.5° 10 kcal/mol", insert -- -9.5 kcal/mol --.

IN THE SOURCE CODE

Column 40:
Line 57, after "Print #1;", delete " ", insert -- ":" --.

UNITED STATES PATENT AND TRADEMARK OFFICE
CERTIFICATE OF CORRECTION

PATENT NO. : 6,181,966 B1
DATED : February 6, 2001
INVENTOR(S) : Donald M. Gray et al.

It is certified that error appears in the above-identified patent and that said Letters Patent is hereby corrected as shown below:

<u>Column 40:</u>
Line 61, after "header <>", delete " ", insert -- ":" --.

<u>Column 41:</u>
Line 41, line 5, delete "nmalength", insert -- mrnalength --.

<u>Column 47:</u>
Line 36, delete "Cuarray (X)", insert -- CUarray (X) --.

<u>Column 49:</u>
Line 56, delete black line "▫▫▫▫▫▫▫"

<u>Column 51:</u>
Line 10, delete "Gcarray (q)", insert —Gcarray (q) --.

<u>Column 52:</u>
Line 48, delete "in RNA target", insert -- in mRNA target --.

<u>Column 53:</u>
Line 50, delete "Global mrnalangth", insert -- Global mrnalength --.

<u>Column 53:</u>
At the end of the Source Code, below "Global h", insert - Global ist As String --.

UNITED STATES PATENT AND TRADEMARK OFFICE
CERTIFICATE OF CORRECTION

PATENT NO. : 6,181,966 B1
DATED : February 6, 2001
INVENTOR(S) : Donald M. Gray et al.

It is certified that error appears in the above-identified patent and that said Letters Patent is hereby corrected as shown below:

IN THE REFERENCES

Column 54:
Line 52, after "2829-2834", insert --, 1992.--.

IN THE CLAIMS

Column 72:
Line 30, claim 27, after "nearest-neighbor", delete "neighbor".

IN THE DRAWINGS

In the top half of Figure 5, after "CALCULATED MELTING TEMPERATURE (DEG. C)", delete "mRNAL LENGTH", insert --mRNA LENGTH--.

Signed and Sealed this

Twelfth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,181,966 B1
DATED : January 30, 2001
INVENTOR(S) : Indra B. Nigam It is certified that error appears in the above-identified patent and that said Letters Patent is hereby corrected as shown below:

Title page,
Change the assignee information to read as --Biotronik Mess- und Therapiegeräte GmbH & Co. Ingenieurbüro Berlin, Berlin, Germany--.

Signed and Sealed this

Seventeenth Day of July, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO. : 6,181,966 B1
DATED : January 30, 2001
INVENTOR(S) : Indra B. Nigam

It is certified that error appears in the above-identified patent and that said Letters Patent is hereby corrected as shown below:

This certificate supersedes certificate of correction issued June 12, 2001, the number was erroneously mentioned and should be deleted since no certificate of correction was granted.

Signed and Sealed this

Eleventh Day of December, 2001

*Attest:*

*Attesting Officer*

NICHOLAS P. GODICI
*Acting Director of the United States Patent and Trademark Office*